(12) United States Patent
Durand De Gevigney et al.

(10) Patent No.: US 9,857,313 B2
(45) Date of Patent: Jan. 2, 2018

(54) METHOD AND SYSTEM FOR INSPECTING WAFERS FOR ELECTRONICS, OPTICS OR OPTOELECTRONICS

(71) Applicant: UNITY SEMICONDUCTOR, Monbonnot-Saint-Martin (FR)

(72) Inventors: Mayeul Durand De Gevigney, Meylan (FR); Philippe Gastaldo, Pontcharra (FR)

(73) Assignee: UNITY SEMICONDUCTOR, Montbonnot-Saint-Martin (FR)

( * ) Notice: Subject to any disclaimer, the term of this patent is extended or adjusted under 35 U.S.C. 154(b) by 0 days.

(21) Appl. No.: 15/515,227

(22) PCT Filed: Sep. 29, 2015

(86) PCT No.: PCT/EP2015/072364
§ 371 (c)(1),
(2) Date: Mar. 29, 2017

(87) PCT Pub. No.: WO2016/050735
PCT Pub. Date: Apr. 7, 2016

(65) Prior Publication Data
US 2017/0219496 A1    Aug. 3, 2017

(30) Foreign Application Priority Data
Sep. 29, 2014 (FR) ...................... 14 59172

(51) Int. Cl.
*G01N 21/00* (2006.01)
*G01N 21/95* (2006.01)
*G01N 21/88* (2006.01)

(52) U.S. Cl.
CPC ..... *G01N 21/9505* (2013.01); *G01N 21/8806* (2013.01); *G01N 21/8851* (2013.01); *G01N 21/9501* (2013.01); *G01N 2021/8874* (2013.01)

(58) Field of Classification Search
CPC .... G01N 21/00; G01N 21/95; G01N 21/9505; G01N 21/9501
(Continued)

(56) References Cited

U.S. PATENT DOCUMENTS 4,030,830 A   6/1977  Holly
5,148,229 A   9/1992  Wiseall
(Continued)

FOREIGN PATENT DOCUMENTS

WO   2009/112704 A1   9/2009

OTHER PUBLICATIONS

International Search Report from International Patent Application No. PCT/EP2015/072364, dated Nov. 27, 2015.
(Continued)

*Primary Examiner* — Roy M Punnoose
(74) *Attorney, Agent, or Firm* — Greer, Burns & Crain, Ltd.

(57) ABSTRACT

A method for inspecting a wafer, includes:
  rotating the wafer about an axis of the wafer,
  emitting from a light source, two pairs of incident coherent light beams, each pair forming, at the intersection between the two beams, a measurement volume,
  a portion of the main wafer surface passing through each of the measurement volumes during the rotation,
  collecting a light beam scattered by the wafer surface,
  capturing the collected light and emitting an electrical signal representing the variation in the collected light intensity,
  detecting in the signal, a frequency, being the time signature of a defect through a respective measurement volume,
  for each detected signature, determining a visibility parameter,
  on the basis of the visibility determined, obtaining an item of information on the size of the defect, and
  cross-checking the items of information to determine the size of the defect.

13 Claims, 6 Drawing Sheets

(58) Field of Classification Search
USPC .................................................. 356/237.5
See application file for complete search history.

(56) References Cited

U.S. PATENT DOCUMENTS

| 5,875,029 A * | 2/1999 | Jann ....................... G01N 21/94 |
| | | 356/237.2 |
| 2002/0191179 A1 | 12/2002 | Tukker et al. |
| 2009/0195786 A1* | 8/2009 | Gastaldo ............ G01N 21/8806 |
| | | 356/477 |

OTHER PUBLICATIONS

Written Opinion from International Patent Application No. PCT/EP2015/072364, dated Nov. 27, 2015.

Farmer, W.M., "Measurement of Particle Size, Number Density, and Velocity Using a Laser Interferometer" Applied Optics (1972), 11(11), p. 2603-2612. (Abstract only).

Tanner, L. H., "A Study of Fringe Clarity in Laser Interferometry and Holography" Journal of Physics E: Scientific Instruments (1968), 1(5). (Abstract Only).

* cited by examiner

Prior Art

METHOD AND SYSTEM FOR INSPECTING WAFERS FOR ELECTRONICS, OPTICS OR OPTOELECTRONICS

BACKGROUND

The present invention relates to a method and a system for inspecting wafers for electronics, optics or optoelectronics.

During the manufacture and use of wafers for electronics, optics or optoelectronics, it is usual to carry out an inspection of the surface of each wafer so as to detect any defects.

On account of the very small size of the defects to be detected, a visual inspection by an operator is not sufficient.

Furthermore, the inspection is generally intended not only to discover the presence or absence of defects, but also to provide qualitative and/or quantitative information on said defects, such as their location, their size and/or their nature, for example.

Inspection systems have thus been developed with a view to detecting increasingly small defects and to provide all required information on the nature, the size, the location, etc. of said defects.

These systems must also allow a duration of inspection of each wafer that is sufficiently short so as not to adversely affect production speeds.

Document WO 2009/112704 describes a system for inspecting semi-conductor wafers implementing Laser Doppler Velocimetry (LDV). As shown in FIG. 1, this system comprises a light source 20 and an interferometric device 30 coupled with the light source arranged facing the surface S of the wafer 2 for inspection, which is actuated by a movement. Said interferometric device comprises a light guide the input of which is coupled with the light source and comprising two branches for dividing the beam originating from the light source into two incident beams. At the output of the light guide, the two branches are oriented in relation to one another so as to form, at the intersection between the two beams, a measurement volume comprising a plurality of parallel fringes. The system also comprises an optical fibre 40 arranged between the surface of the wafer and a detection module 50, so as to guide the light backscattered by the surface of the wafer towards the detection module.

Document WO 02/39099 describes another system for inspecting semi-conductor wafers relying on Laser Doppler Velocimetry.

The presence of a defect on the surface of the wafer is indicated, when this defect crosses the interference fringes, by the scattering of a Doppler burst measured by the detection module. A Doppler burst is a signal that has a double frequency component: a low-frequency component, forming the envelope of the signal, corresponding to the mean light intensity scattered by the defect, and a high-frequency component, corresponding to the Doppler frequency containing the information on the velocity of the defect. The Doppler frequency $f_D$ is linked to the velocity v of movement of the defect in the direction perpendicular to the interference fringes and to the distance $\Delta$ between the interference fringes (or inter-fringe distances) by the relationship $v = f^* \Delta$.

FIG. 2 shows a Doppler burst due to a defect passing through the interference zone, expressed in the form of an electrical voltage (in Volts) at the output of the detection module as a function of time.

On the basis of such a Doppler burst, it is possible to determine the size of the defects detected on the surface of the wafer.

In this respect, reference may be made to the publication by W. M. Farmer entitled "Measurement of Particle Size, Number Density, and Velocity Using a Laser Interferometer", which presents a model of the visibility of a particle as a function of the particle size.

Thus, for a pattern of given interference fringes, the relationship between the size of a defect compared to a sphere, which is defined as the diameter of the sphere, and the visibility determined according to the above formula, is given by a curve of the type shown in FIG. 3.

It is noted that, for a visibility greater than 0.15, the curve of FIG. 3 provides a unique defect size corresponding to a given visibility value.

However, for a visibility less than 0.15, the curve shows "bounces", indicating the fact that a single visibility value can correspond to several defect sizes. Thus, in the example in FIG. 3, a visibility of 0.1 corresponds to three radii of a sphere: 0.83 µm, 1.12 µm and 1.45 µm.

In such a case, the problem then arises of determining, among these different possible sizes, the actual size of the defect present on the wafer.

In particular, this technique does not allow measurement of the size of defects of very different sizes. In fact, as shown in FIG. 3, it is not possible to determine the size of defects having a size larger than 0.9 µm (corresponding to a visibility less than 0.15).

Now, the size of the defects capable of being detected on a wafer extends over a wide range of dimensions, typically from a few tens of nanometers to a few hundred micrometers.

Another drawback of the technique based on the curve in FIG. 3 is that, for some defect sizes (for example a radius of 0.95 µm), the visibility is zero, i.e. no Doppler burst is produced. Consequently, a defect of this size cannot be detected.

SUMMARY

A purpose of the invention is to overcome the aforementioned drawbacks and to define a system and a method for inspecting wafers that make it possible to detect all of the defects that may be present on the wafer having a size larger than a few tens of nanometers, and to determine with certainty the size of each detected defect. This system and this method must also have improved detection dynamics with respect to the existing systems and methods, i.e. a greater capacity to detect a large number of defects and to assess their size within a reduced timescale over a broad range of defect sizes.

According to the invention, a method is proposed for inspecting a wafer for electronics, optics or optoelectronics, comprising:

rotating the wafer about an axis of symmetry perpendicular to a main surface of said wafer, emitting, from at least one light source, at least two pairs of incident coherent light beams, each pair being arranged in order to form, at the intersection between the two beams, a respective measurement volume containing interference fringes having an inter-fringe distance different from that of another measurement volume, at least a portion of the main surface of the wafer passing through each of said measurement volumes during the rotation of the wafer, collecting a light beam scattered by the surface of the wafer, capturing the collected light and emitting an electrical signal representing the variation in the light intensity of the collected light as a function of time, detecting, in said signal, a frequency component in the variation of the intensity of said collected light, said frequency being the time signature of the passage of a defect through a respective measurement volume, for each detected signature, determining a parameter, called visibility of the defect, dependent on the inter-fringe distance of the respective measurement volume and the size of the defect and given by the following formula, determined on the basis of a Doppler signal due to a defect passing through the measurement volume and expressed in the form of an electrical voltage as a function of time:

$$\frac{I_{max} - I_{min}}{I_{max} + I_{min} - 2*\text{Offset}}$$

where Imax and Imin define the minimum electrical voltage and the maximum electrical voltage defining the peak of said Doppler signal and Offset is that between the mean value of the Doppler signal and an axis corresponding to a zero electrical voltage, on the basis of the visibility determined for each measurement volume, obtaining a respective item of information on the size of said defect, cross-checking the items of information obtained for each measurement volume in order to determine the size of the defect.

Particularly advantageously, obtaining an item of information on the size of the defect comprises:

calculating the visibility of the defect in each measurement volume, for each measurement volume, on the basis of a visibility reference curve as a function of the size of the defect for the respective inter-fringe distance, determining one or more possible sizes for the defect.

Preferably, said method comprises the filtering of the signal with a band-pass filter the pass-band of which incorporates the Doppler frequency associated with each measurement volume.

According to an embodiment, said measurement volumes are at least partially superimposed.

According to another embodiment, said measurement volumes follow one another along the path of rotation of the wafer.

Particularly advantageously, the method also comprises a radial movement of said measurement volumes with respect to the wafer.

As a general rule, the fringes of each measurement volume are oriented transversally to the path of rotation of the wafer.

According to a particularly advantageous embodiment, the interferometric device is an integrated optical device comprising a light guide the input of which is coupled with the light source and which is divided into two pairs of branches, the output of which is oriented in order to form a respective measurement volume at the intersection of the two beams of each pair.

According to an embodiment of the invention, the wafer is at least partially transparent vis-à-vis the wavelength of the light source and each measurement volume extends into a region of the wafer having a thickness less than the thickness of said wafer.

A further subject relates to a system for inspecting wafers for electronics, optics or optoelectronics, comprising:

a device for driving a wafer in rotation about an axis of symmetry perpendicular to a main surface of said wafer, at least one light source, at least one interferometric device coupled with the light source in order to divide the beam emitted by said source into two beams and in order to form, at the intersection between the two beams, a respective measurement volume containing interference fringes, having an inter-fringe distance that is different from that of another measurement volume, a device for the collection of light scattered by the wafer, a device for capturing the collected light configured in order to emit an electrical signal representing the variation in the light intensity of said collected light as a function of time, a processing device configured in order to:

detect, in said signal, a frequency component in the variation of the intensity of said collected light, said frequency being the time signature of the passage of a defect through a respective measurement volume, for each detected signature, determine a parameter, called visibility of the defect, dependent on the inter-fringe distance of the respective measurement volume and the size of the defect, and given by the following formula, determined on the basis of a Doppler signal due to a defect passing through the measurement volume and expressed in the form of an electrical voltage as a function of time:

$$\frac{I_{max} - I_{min}}{I_{max} + I_{min} - 2*\text{Offset}}$$

where Imax and Imin define the minimum electrical voltage and the maximum electrical voltage defining the peak of said Doppler signal and Offset is that between the mean value of the Doppler signal and an axis corresponding to a zero electrical voltage.

obtain, on the basis of the visibility determined for each measurement volume, a respective item of information on the size of said defect, cross-check the information obtained for each measurement volume in order to determine the size of the defect.

According to an advantageous embodiment, said system comprises a single light source and a single interferometric device in order to form all the measurement volumes.

According to a preferred embodiment, in which the interferometric device is in the form of an integrated optical device comprising a light guide the input of which is coupled with the light source and which is divided into two pairs of branches, the output of which is oriented in order to form a respective measurement volume at the intersection of the two beams of each pair.

Particularly advantageously, the system also comprises an arm for moving the interferometric device and the device for the collection of the scattered beam in translational motion in a radial direction.

BRIEF DESCRIPTION OF THE DRAWINGS

Other characteristics and advantages will become apparent from the detailed description that follows, with reference to the attached drawings in which.

In the interests of clarity, the figures are not necessarily to scale.

DETAILED DESCRIPTION

The present invention relates to any wafer intended for use in the field of electronics, optics or optoelectronics. In particular, the wafer can comprise at least one of the following materials: Si, Ge, GaN, SiC, glass, quartz, sapphire, GaAs (non-limitative list).

Furthermore, the material of the wafer may or may not be partially transparent at the wavelength of the light source of the inspection system. In fact, according to a particularly advantageous embodiment that will be described in detail below, the inspection system provides a controlled depth of field, making it possible to control the position of the measurement volume with respect to the wafer, by arranging for the region of the wafer in which the measurement volume extends to have a thickness that is less than the thickness of the wafer. In this way it is ensured that the detected defects are located on the surface for inspection or its close neighbourhood, and not on the opposite surface.

In order to allow the unambiguous determination of the size of a detected defect and to make each defect visible regardless of its size within a range of a few tens of nanometers to a few hundred micrometers, the invention proposes to form at least two measurement volumes containing interference fringes and each having a different inter-fringe distance.

The measurement volumes are arranged with respect to one another such that a defect of the wafer passes into each of the measurement volumes and generates, if appropriate, a respective Doppler burst.

Figure 4:
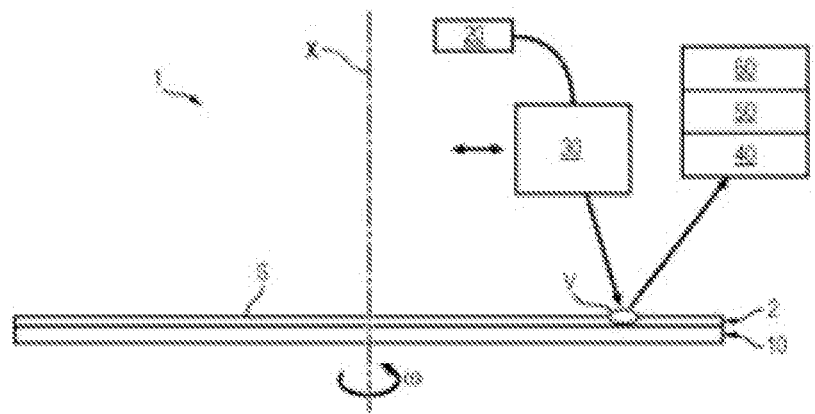
FIG. 4 is a schematic diagram of the inspection system according to an embodiment of the invention.

FIG. 4 is a schematic diagram of an inspection system 1 utilizing such measurement volumes.

The system comprises a support 10 intended to receive a wafer 2 for inspection and to drive it in rotation about an axis of symmetry X perpendicular to a main surface S of said wafer. Generally, the wafer has a circular shape but the invention is applicable to any other shape.

The wafer 2 is held on the support 10 by any appropriate means, such as electrostatic means, mechanical means, etc.

The mechanism for rotating the support is known per se and therefore will not be described in detail.

The support 10 comprises one or more encoders (not shown) making it possible to know the angular position of the wafer at any moment.

The inspection system 1 also comprises a light source 20.

The light source 20 is typically a distributed feedback (DFB) laser.

The light source is coupled with an interferometric device 30 that will be described in detail with reference to FIG. 5.

The interferometric device 30 is designed in order to form at least two measurement volumes (only one of which is shown diagrammatically in FIG. 4 under the reference V) having different inter-fringe distances. These measurement volumes can be totally or partially within a single space. As will be explained below with reference to FIG. 6, the inter-fringe distances are chosen so that the visibility curves associated with each of these measurement volumes are sufficiently different from one another so that a defect that is not visible in one of the measurement volumes is visible in the other measurement volume, and in order to remove any ambiguities relating to the size of the detected defects.

It can be envisaged for the inspection system to comprise several interferometric devices each coupled to a light source in order to form a respective measurement volume, but this embodiment is less advantageous in terms of bulk and cost. As a result, preferably, the inspection system comprises a single light source and a single interferometric device suitable for forming the different measurement volumes.

The inspection system comprises in addition a device 40 for collection of the light backscattered by the surface of the wafer. This device 40 can comprise an optical fibre, preferably with a large core diameter (i.e. typically between 100 and 1000 µm in diameter), the input of which is arranged facing the surface of the wafer, close to the measurement volumes, and the output of which is coupled with a device 50 for capturing collected light in order to emit an electrical signal representing the variation in the light intensity of the collected light as a function of time. Said device 50 typically comprises a photodetector.

Preferably, the interferometric device 30 and the device 40 for the collection of the backscattered light are firmly fixed together. In fact, the input of the collection device 40 must be positioned in an appropriate manner with respect to the measurement volumes in order to receive the light backscattered by the wafer.

Finally, the inspection system 1 comprises a processing device 60 configured in order to detect, in said signal, a frequency component corresponding to the Doppler frequency.

The processing device 60 is advantageously coupled with an interface (not shown) making it possible for a user to access the results so as in particular to display them, record them and/or print them.

In the case where the wafer is at least partially transparent vis-à-vis the wavelength of the light source, arrangements are made so that the region in which each measurement volume extends has a thickness less than that of the wafer. The thickness of said region is preferably less than or equal to 90% of the thickness of the wafer. For example, for a wafer of 500 µm to 1 mm in thickness, arrangements are made so that the measurement volumes extend into a region of the wafer having a thickness less than or equal to 100 µm.

The dimension of the measurement volume is characteristic of the interferometric device and is defined by the angle between the two branches of the light guide in which the light beam emitted by the source propagates and by the numerical aperture of said branches.

It will be noted in this respect that the inspection systems currently available on the market do not allow satisfactory inspection of transparent wafers.

In fact, in the case of the systems based on the dark field inspection technique, the incident beam passes through the thickness of the wafer and any defect, whether present on the surface to be inspected, on the opposite surface or in the thickness of the substrate, generates a scattered light. It is therefore impossible, with such a system, to know whether each detected defect is located on the surface for inspection or not.

Furthermore, the company KLA-Tencor proposes a system for inspecting transparent wafers called Candela™, of the dark field illumination and confocal laser detection type. However, this system is particularly difficult to focus due to the accuracy of positioning required for the confocal detection, and therefore does not provide repeatable results.

The system implemented in the invention overcomes the constraints associated with the dark field technique and with the confocal detection technique by detecting the defects by using a frequency signal, which can only be emitted by defects passing through a measurement volume. In such a system, the positioning of the interferometric device must therefore be adjusted accurately with respect to the surface of the wafer for inspection, but the device for the collection of the backscattered light does not require an equally high positioning accuracy since the restriction of the measurement volume, and thus the detection, is carried out via the Doppler frequency.

Furthermore, in order to inspect transparent wafers, an integrated optical device such as that described below is preferably chosen in order to produce the interferometric device. Such a device in fact makes it possible to control the depth of field of the inspection system. On the other hand, measurement of the size by a visibility calculation is independent of the position of the defect in the measurement volume.

In order to inspect a wafer, said wafer 2 is put in place on the support 10 and the support is driven in rotation at a controlled angular velocity go. By means of the encoders present on the support 10, the angular position of a given point of the wafer is known at each moment. The velocity of rotation of the wafer is typically of the order of 5000 rpm.

In the inspection system 1, the interferometric device 30 is arranged facing a main surface of the wafer 2, on an arm (not shown) suitable for moving said device 30 in a radial direction. Thus, taking account of the rotation of the wafer, it is possible to successively sweep the entire surface of the wafer with the measurement volumes by moving the interferometric device radially in translation as well as the device for collection of the backscattered light.

The two measurement volumes are formed on the same side of the wafer, in order to ensure that a defect passes through all the measurement volumes. The interference fringes of each measurement volume are oriented transversally with respect to the path of rotation of the wafer, so as to be passed through by the defects. The inclination between the fringes and the path of rotation of the wafer can be perpendicular or according to another non-zero angle.

Figure 1:
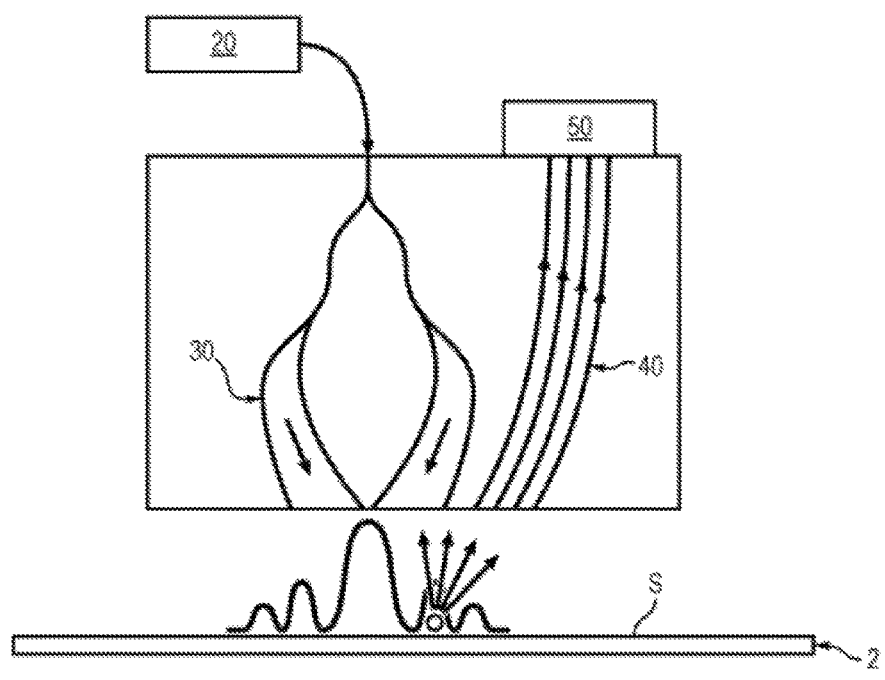
FIG. 1 is a schematic diagram of an inspection system based on laser Doppler velocimetry, as described in the document WO 2009/112704.
Figure 2:
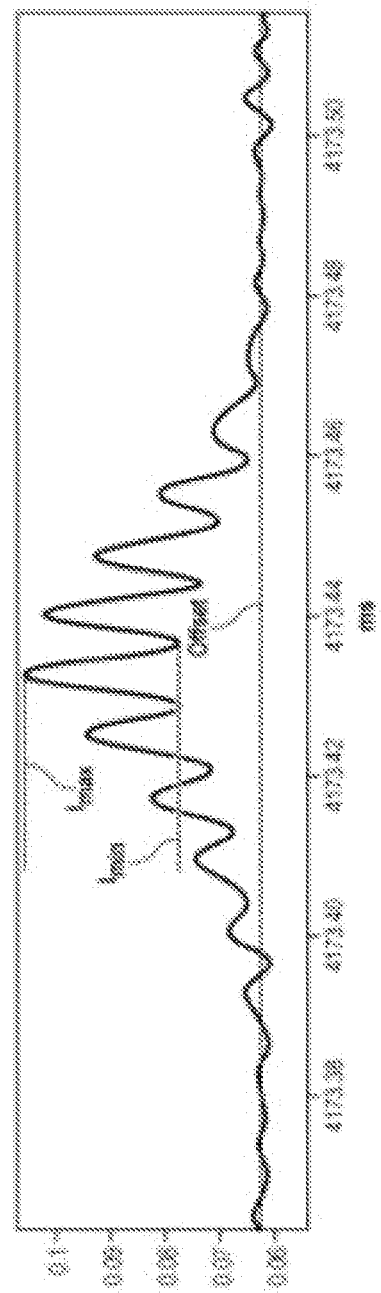
FIG. 2 shows an example of a Doppler burst.

According to the aforementioned principle of the method of W. M. Farmer, for each measurement volume the visibility of a detected defect is calculated by the formula:

$$\frac{I_{max} - I_{min}}{I_{max} + I_{min} - 2*\text{Offset}}$$

where Imax and Imin (in V) define the minimum electrical voltage and the maximum electrical voltage defining the peak of the Doppler burst and Offset (in V) is that between the mean value of the signal and the x-axis corresponding to a zero electrical voltage (cf FIG. 2). This offset, which does not appear in the formula of W. M. Farmer, is linked to the measurement conditions, and takes account of the fact that even in the absence of a defect, a small quantity of light scattered by the surface can be detected.

Figure 3:
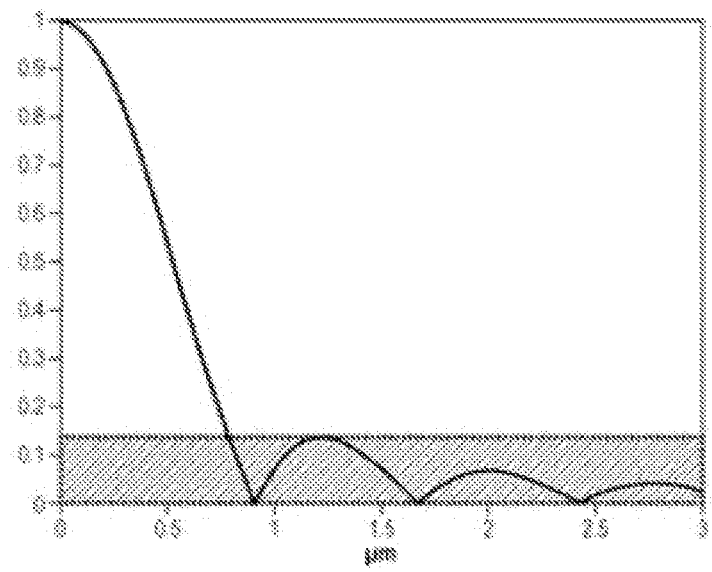
FIG. 3 is a diagram showing the visibility (variable without units) of a defect compared to a sphere as a function of its size (in the case in question the radius of the sphere expressed in micrometers)

In addition, a plurality of reference curves of the type of that in FIG. 3 are stored in a memory of the processing device, each reference curve defining the visibility of a defect in a respective measurement volume as a function of the size of the defect.

In an embodiment of the invention, the measurement volumes follow one another along the path of rotation of the wafer, at the same radial distance from the axis of rotation of the wafer. Thus, the defects pass successively through the different measurement volumes during the rotation of the wafer.

According to another embodiment of the invention, the measurement volumes are at least partially superimposed. In fact, subject to implementing band-pass filtering integrating the Doppler frequency associated with each inter-fringe distance and therefore with each measurement volume, the signal emitted by the photodetector contains only the information linked to these measurement volumes and makes it possible for them to be distinguished. By "integrating" is meant here that the pass-band of the filter comprises the Doppler frequency and a small frequency range around this Doppler frequency.

Figure 5A:
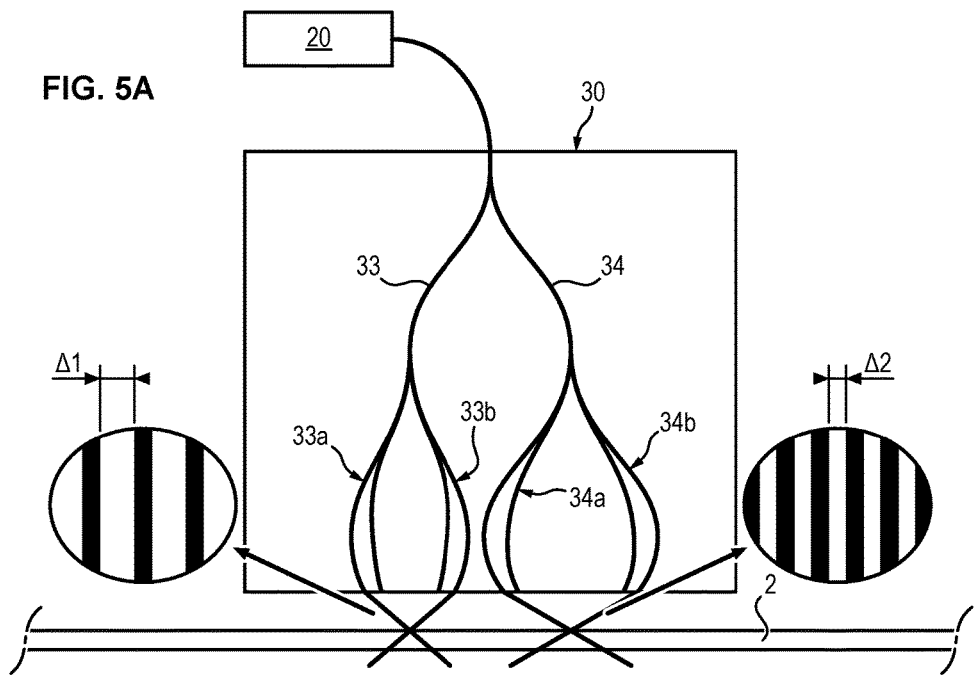
FIGS. 5A and 5B are schematic drawings of the interferometric device according to two embodiments of the invention.
Figure 5B:
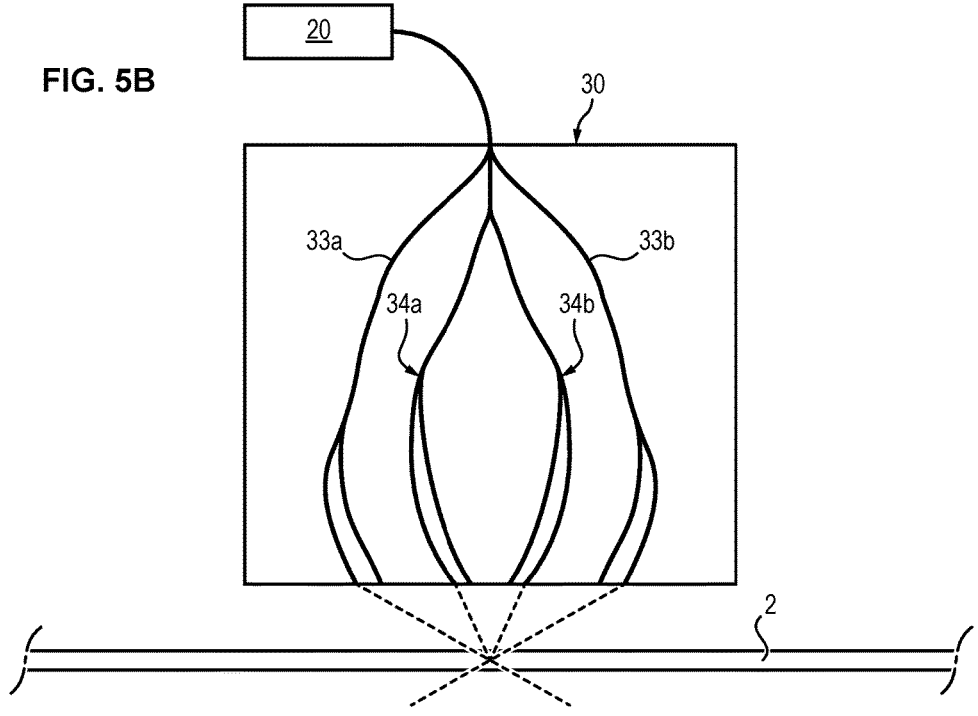

FIGS. 5A and 5B are schematic drawings of the two embodiments of an interferometric device making it possible to form two measurement volumes containing interference fringes, each having a different inter-fringe distance. In the case of FIG. 5A, the measurement volumes are adjacent; in the case of FIG. 5B, the measurement volumes are at least partially superimposed.

This device 30 comprises a light guide 31 the input 32 of which is coupled with the light source 20 and comprising two symmetrical main branches 33, 34 for dividing the beam originating from the light source into two incident beams.

Each branch 33, 34 is itself divided into two symmetrical secondary branches, respectively 33a, 33b and 34a, 34b.

At its end, each secondary branch has an expanded portion intended to widen the beam while retaining its Gaussian profile.

At the output of the light guide, the secondary branches of each pair are oriented in relation to one another so as to form, at the intersection between the two beams, a measurement volume containing parallel interference fringes. As shown diagrammatically in FIG. 5A, the pair 33a, 33b forms a measurement volume the inter-fringe distance of which has a value Δ1 and the pair 34a, 34b forms a measurement volume the inter-fringe distance of which has a value Δ2 different from Δ1.

The device in FIG. 5B follows the same principle as that in FIG. 5A, but the fringes have not been shown in order to simplify the figure. In this embodiment, the different branches are symmetrically interleaved so that the measurement volumes created at the output of said branches substantially coincide.

Particularly advantageously, the interferometric device is in the form of an integrated sensor constituted by a single piece and ensuring both the separation of the beam emitted by the light source and the transmission of the pairs of branches of the beam in order to form the interference volumes at the output of the sensor. It is noted that an integrated optical device is an optical device produced by microelectronic techniques.

The article "Integrated Laser Doppler Velocimeter for Fluid Velocity and Wall Friction Measurements" by P. Lemaitre-Auger et al. describes such a sensor (which in this case has a single main branch and two secondary branches, so as to form a single measurement volume). Such a device is produced in particular by the company A2 Photonic Sensors and marketed under the reference i-LDA™.

The same method of manufacture as that described in the aforementioned article can be implemented in order to integrate several light guides within the sensor in order to form several measurement volumes.

By way of example, the integrated optical device can be produced by ion exchange on a glass substrate. This process generally comprises:
providing a glass substrate,
depositing a metallic masking layer onto said glass substrate,
depositing a polymer layer onto the metallic layer,
transferring by photolithography a pattern defining the shape of the light guide onto the polymer layer,
chemical etching of the metallic masking layer using a chemical process in the zones left exposed by the polymer mask,
removing the polymer mask,
immersing the substrate covered with the etched metallic masking layer in an ion bath (for example a potassium nitrate bath),
exchanging ions present in the bath (for example potassium ions) and ions contained in the glass (for example sodium ions) through zones of the substrate that are not covered by the metallic masking layer, the latter blocking the passage of the ions.

On account of the difference in size between the ions present in the bath and the ions present in the glass, the ion exchange generates local mechanical stresses in the glass substrate which increase the refractive index of the glass. The aforementioned optical waveguide is obtained in this way.

The metallic masking layer is then removed and optionally a protective layer, for example of $SiO_2$, is deposited. Finally, the edges of the substrate are cut out and they are finely polished.

There are other processes for the manufacture of integrated optical devices and a person skilled in the art may choose from the microelectronic technologies at their disposal in order to design the integrated optical device.

Optionally, the optical device may also be combined with an optical fibre making it possible to collect the backscattered light.

An advantage of this integrated device is its robustness and its stability. In particular, unlike a system produced by other technologies such as micro-optics or optical fibres, the compact nature of the integrated device and the integration of the various components means that it is not sensitive to vibration and temperature gradients.

Advantageously, when it is desired to inspect wafers that are least partially
transparent with respect to the wavelength of the light source, arrangements are made to ensure that the thickness of the region of the wafer in which the measurement volume extends is less than the thickness of the wafer (this region including a portion of the surface area to be inspected). The thickness of said region is preferably less than or equal 25 to 90% of the thickness of the wafer. For example, for a wafer of 500 μm to 1 mm in thickness, arrangements are made so that the measurement volume extends into a region of the wafer having a thickness less than or equal to 100 μm. The dimension of the measurement volume is characteristic of the interferometric device and is defined by the angle between the two branches of the light guide in which the light beam emitted by the source propagates and by the numerical aperture of said branches. These characteristics are thus set during the manufacture of the integrated optical device, which makes it possible to ensure good control of the performances of the system during its mass production.

Thus, it is possible to limit this measurement volume to the surface of the wafer or to a region of the neighbourhood of said surface. In this way it is ensured that the detected defects are located on the surface to be inspected or its close neighbourhood, and not on the opposite surface of the wafer.

An integrated optical device has an additional advantage in this context, given that its stability makes it possible to avoid a depth-of-field error. The control of the depth of field permitted by the integrated device thus facilitates the inspection of transparent wafers by laser Doppler velocimetry It will be noted that by contrast, the control of the depth of field assumes a lesser importance for inspecting an opaque wafer, given that, since the measurement volume does not penetrate into the thickness of such a wafer, it is sufficient for a portion of the surface of the wafer to pass through the measurement volume in order to allow the inspection of said surface.

As stated in the aforementioned article, the inter-fringe distance depends on the wavelength of the light source, the optical index of the lightguide and the angle between the two secondary branches. For a given wavelength of the light source, the inter-fringe distance is thus fixed during the manufacture of the integrated optical device.

Figure 6:
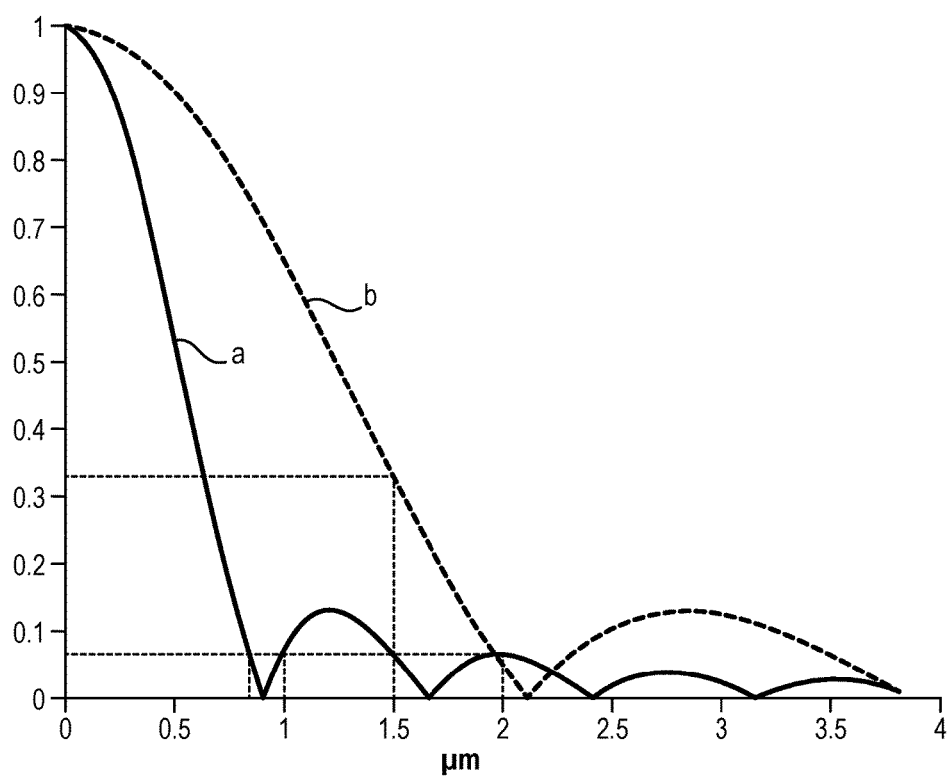
FIG. 6 is a diagram showing the visibility (without units) of a defect compared to a sphere as a function of its size (radius of the sphere in µm), for an inspection system according to the invention.

FIG. 6 shows two examples of visibility curves as a function of the size of the defect for two different inter-fringe distances.

The curve (a) corresponds substantially to the curve in FIG. 3.

It is noted that curve (b) has fewer "bounces" corresponding to zero visibility than curve (a), and that said points of zero visibility do not coincide with the points of zero visibility of curve (a).

Thus, if a defect has zero visibility in the measurement volume corresponding to curve (a), it cannot be detected via curve (a); on the other hand, as it has a visibility that is non-zero in the measurement volume corresponding to curve (b), it can be detected via said curve (b).

For example, a defect of radius 1.7 μm has zero visibility on curve (a) but a visibility of around 0.22 on curve (b) and thus will be detectable on curve (b).

Furthermore, this offset of the visibility curves makes it possible to remove the ambiguities on the size of the detected defects by cross-checking the information supplied by both curves. In fact, by choosing visibility curves that are sufficiently distant from one another, a visibility corresponding to several possible defect sizes on one of the curves will only correspond to one defect size on the other curve.

For example, a defect of 1.5 μm has a visibility of 0.07 on curve (a). Now, on curve (a), a visibility of 0.07 corresponds to four sizes of defect. 0.8 μm, 1 μm, 1.5 μm and 2 μm; this single visibility value therefore does not allow a conclusion to be drawn on the size of the detected defect. On the other hand, on curve (b), this same defect of radius 1.5 μm has a visibility of 0.33. As a result, knowledge of the visibilities of 0.07 and 0.33 makes it possible to conclude unambiguously that the radius of the detected defect is 1.5 μm.

A person skilled in the art is able to determine the inter-fringe distance of each measurement volume in order to allow the determination of the size of a defect throughout the entire extent of the size to be detected. On the basis of curves of the type of that in FIG. 3, which can be obtained by simulation according to the method described by W. M. Farmer, a person skilled in the art will seek to have a sufficiently high visibility for each measurement volume and avoid the case where the combination of the items of information collected based on each measurement volume may correspond to several sizes of defects.

Although up to this point embodiments have been described with two measurement volumes having different inter-fringe distances, the invention can more generally be implemented with an integer N greater than or equal to two measurement volumes each having a specific inter-fringe distance. With three measurement volumes or more, in fact the accuracy of determination of the size of the defects will be further increased.

Figure 7:
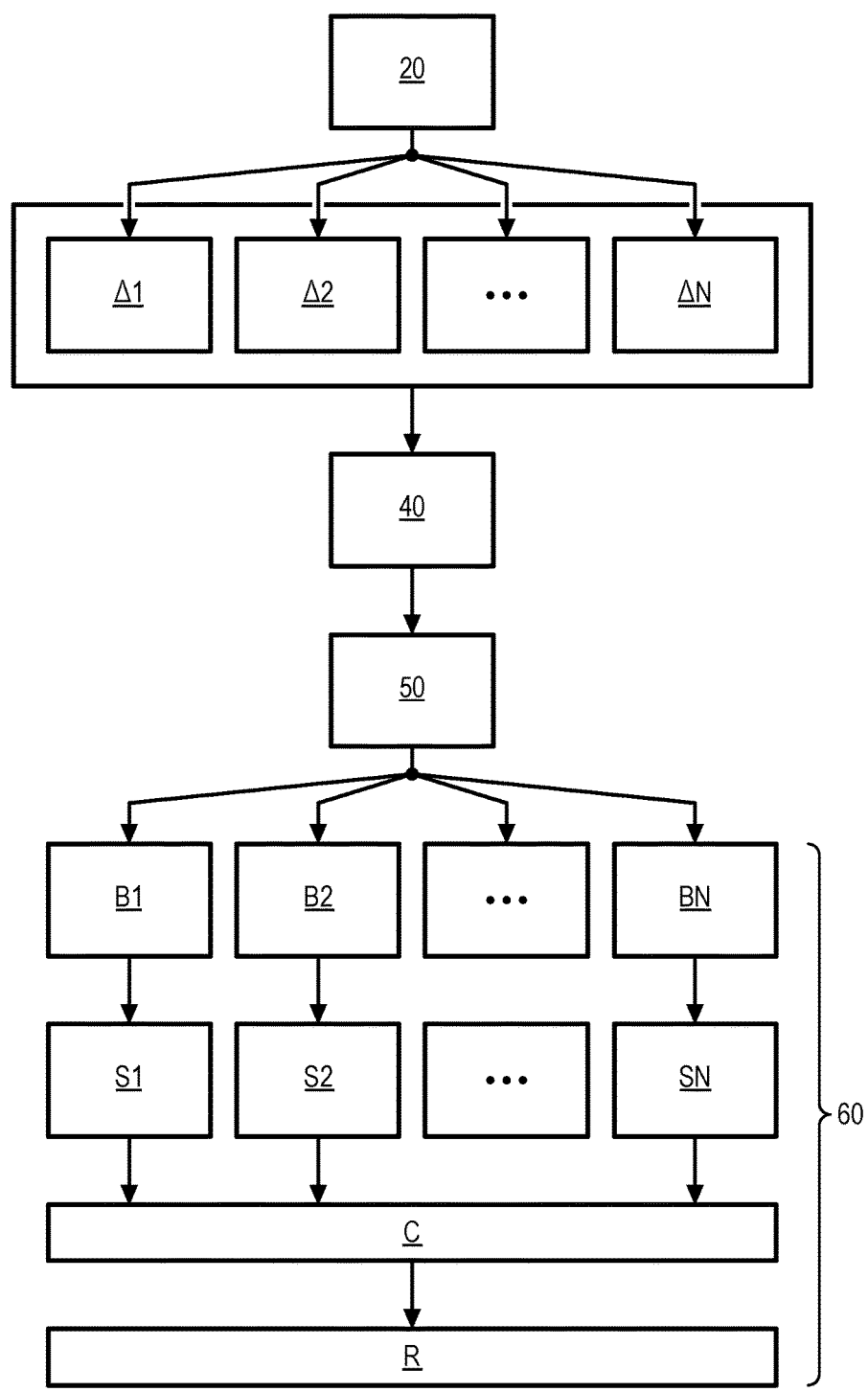
FIG. 7 shows the principle of the detection of defects implementing a number N greater than or equal to two measurement volumes.

FIG. 7 is a logic diagram showing the sequence of detection of defects with a number N of measurement volumes greater than two.

The light source 20 is coupled to the input of the interferometric device which comprises N pairs of secondary branches, each pair being designed so as to have a different inter-fringe distance $\Delta 1, \Delta 2, \ldots, \Delta N$.

The device 40 for the collection of the backscattered light is common to the set of measurement volumes, as is the capturing device 50 and the processing device 60.

In the processing device 60, the signal supplied by the capturing device 50 is filtered by N band-pass filters each having a different pass-band B1, B2, . . . BN, incorporating the Doppler frequency associated with a respective inter-fringe distance $\Delta 1, \Delta 2, \ldots, \Delta N$.

As a result, the filtered signal provides N items of information S1, S2, . . . SN on the size of the detected defects. In the case where a defect is not visible in one of the measurement volumes, the corresponding information is an absence of a defect. In the case where a defect has a visibility associated with different possible sizes, the corresponding information is the set of possible sizes.

The set of information S1, S2, . . . , SN is then combined in order to allow, by cross-checking, unambiguous determination of the size of each detected defect (step shown diagrammatically by block C).

The detection device then provides a report R on the detected defects, indicating the size and the position of each defect.

REFERENCES

WO 2009/112704
WO 02/39099
Measurement of Particle Size, Number Density, and Velocity Using a Laser Interferometer, W. M. Farmer, Applied Optics, Vol. 11, No. 11, November 1972, pp. 2603-2612
Integrated Laser Doppler Velocimeter for Fluid Velocity and Wall Friction Measurements, P. Lemaitre-Auger, A. Cartellier, P. Benech and Schanen Duport, Sensors, 2002, Proceedings of IEEE (Vol: 1), pp. 78-82.

The invention claimed is:

1. A method for the inspection of a wafer for electronics, optics or optoelectronics, comprising:
    rotating the wafer about an axis of symmetry perpendicular to a main surface of said wafer;
    emitting, from at least one light source coupled with an interferometric device, at least two pairs of incident coherent light beams, each pair being arranged in order to form, at the intersection between the two beams, a respective measurement volume containing interference fringes having an inter-fringe distance different from that of another measurement volume;
    at least a portion of the main surface of the wafer passing through each of said measurement volumes during the rotation of the wafer;
    collecting at least a portion of the light scattered by said part of the surface of the wafer;
    capturing the collected light and emitting an electrical signal representing the variation in the light intensity of the collected light as a function of time;
    detecting, in said signal, a frequency component in the variation of the light intensity of said collected light, said frequency being the time signature of the passage of a defect through a respective measurement volume;
    for each detected signature, determining a parameter, called visibility of the defect, dependent on the inter-fringe distance of the respective measurement volume and the size of the defect and given by the following formula, determined on the basis of a Doppler signal due to a defect passing through the measurement volume and expressed in the form of an electrical voltage as a function of time:

$$\frac{I_{max} - I_{min}}{I_{max} + I_{min} - 2*\text{Offset}}$$

where Imax and Imin define the minimum electrical voltage and the maximum electrical voltage defining the peak of said Doppler signal and Offset is that between the mean value of the Doppler signal and an axis corresponding to a zero electrical voltage;
    on the basis of the visibility determined for each measurement volume, obtaining a respective item of information on the size of said defect; and
    cross-checking the information obtained for each measurement volume in order to determine the size of the defect.

2. The method according to claim 1, in which obtaining an item of information on the size of the defect comprises:
    calculating the visibility of the defect in each measurement volume,
    for each measurement volume, on the basis of a visibility reference curve as a function of the size of the defect for the respective inter-fringe distance, determining one or more possible sizes for the defect.

3. The method according to claim 1, said method comprising filtering the signal with a band-pass filter the pass-band of which incorporates the Doppler frequency associated with each measurement volume.

4. The method according to claim 1, in which said measurement volumes are at least partially superimposed.

5. The method according to claim 1, in which said measurement volumes follow one another along the path of rotation of the wafer.

6. The method according to claim 1, comprising a radial movement of said measurement volumes with respect to the wafer.

7. The method according to claim 1, in which the fringes of each measurement volume are oriented transversally to the path of rotation of the wafer.

8. The method according to claim 1, in which the interferometric device is an integrated optical device comprising a light guide the input of which is coupled with the light source and which is divided into two pairs of branches, the output of which is oriented in order to form a respective measurement volume at the intersection of the two beams of each pair.

9. The method according to claim 1, in which the wafer is at least partially transparent vis-à-vis the wavelength of the light source and each measurement volume extends into a region of the wafer having a thickness less than the thickness of said wafer.

10. A system for inspecting wafers for electronics, optics or optoelectronics, comprising:
- a device for driving a wafer in rotation about an axis of symmetry perpendicular to a main surface of said wafer;
- at least one light source;
- at least one interferometric device coupled with the light source in order to divide the beam emitted by said source into two pairs of beams and in order to form, at the intersection between two beams of each pair, a respective measurement volume containing interference fringes, having an inter-fringe distance that is different from that of another measurement volume;
- a device for the collection of at least a portion of the light scattered by the surface of the wafer;
- a device for capturing the collected light configured in order to emit an electrical signal representing the variation in the light intensity of said collected light as a function of time;
- a processing device configured in order to:
  - detect, in said signal, a frequency component in the variation of the intensity of said collected light, said frequency being the time signature of the passage of a defect through a respective measurement volume;
  - for each detected signature, determine a parameter, called visibility of the defect, dependent on the inter-fringe distance of the respective measurement volume and the size of the defect, and given by the following formula, determined on the basis of a Doppler signal due to a defect passing through the measurement volume and expressed in the form of an electrical voltage as a function of time:

$$\frac{I_{max} - I_{min}}{I_{max} + I_{min} - 2*\text{Offset}}$$

where Imax and Imin define the minimum electrical voltage and the maximum electrical voltage defining the peak of said Doppler signal and Offset is that between the mean value of the Doppler signal and an axis corresponding to a zero electrical voltage;
  - obtain, on the basis of the visibility determined for each measurement volume, a respective item of information on the size of said defect; and
  - cross-check the information obtained for each measurement volume in order to determine the size of the defect.

11. The system according to claim 10, comprising a single light source and a single interferometric device in order to form all the measurement volumes.

12. The system according to claim 10, in which the interferometric device is in the form of an integrated optical device comprising a light guide the input of which is coupled with the light source and which is divided into two pairs of branches, the output of which is oriented in order to form a respective measurement volume at the intersection of the two beams of each pair.

13. The system according to claim 10, also comprising an arm for moving the interferometric device and the device for the collection of scattered light in translational motion in a radial direction.

* * * * *